(12) United States Patent
Imamoto et al.

(10) Patent No.: US 8,076,480 B2
(45) Date of Patent: Dec. 13, 2011

(54) PROCESS OF PREPARING OPTICALLY ACTIVE ALLYL COMPOUND

(75) Inventors: Tsuneo Imamoto, Chiba (JP); Kazuhiro Yoshida, Chiba (JP); Miwako Nishimura, Chiba (JP); Aya Koide, Chiba (JP)

(73) Assignees: National University Corporation Chiba University, Chiba (JP); Nippon Chemical Industrial Co., Ltd., Tokyo (JP)

( * ) Notice: Subject to any disclaimer, the term of this patent is extended or adjusted under 35 U.S.C. 154(b) by 180 days.

(21) Appl. No.: 12/179,069

(22) Filed: Jul. 24, 2008

(65) Prior Publication Data
US 2009/0030200 A1 Jan. 29, 2009

(30) Foreign Application Priority Data

Jul. 26, 2007 (JP) ................. 2007-195234
Jun. 25, 2008 (JP) ................. 2008-165785

(51) Int. Cl.
*C07D 241/36* (2006.01)
(52) U.S. Cl. ........................................ 544/353
(58) Field of Classification Search ............ 544/353
See application file for complete search history.

(56) References Cited

U.S. PATENT DOCUMENTS

| 2007/0021610 A1 | 1/2007 | Imamoto et al. |
| 2007/0066825 A1 | 3/2007 | Scholz et al. |

FOREIGN PATENT DOCUMENTS

| CN | 1438227 A | 8/2003 |
| JP | 2007-056007 A | 3/2007 |

OTHER PUBLICATIONS

Great Britain Office Action dated Dec. 19, 2008, issued in corresponding Great Britain Patent Application No. GB0813271.4.
Tsarev, Vasily N. et al.; "Novel Highly Efficient P-Chiral Ferrocenylimino Diamidophosphite Ligands for Pd-Catalysed Asymmetric Allylation"; European Journal of Organic Chemistry, vol. 10, pp. 2097-2105, 2005.
Nakano, Hiroto et al.; "Polymer-supported chiral phosphinooxazolidine ligands for palladium-catalyzed asymmetric allylic alkylations and Diels-Alder reactions"; Tetrahedron: Asymmetry, vol. 16, pp. 2133-2140, 2005.
Braga, Antonio L. et al.; "New Simple Chiral Phosphine Oxazolidine Ligands: Easy Synthesis and Application in the Palladium-Catalyzed Asymmetric Allylic Alkylation"; Synlett, vol. 8, pp. 1331-1333, 2005.
Chelucci, Giogio et al.; "Chiral 5-(diphenylphosphanyl)-1,2,3,4-tetrahydroacridines: new N,P-ligands for asymmetric catalysis"; Tetrahedron Letters, vol. 46, pp. 3493-3496, 2005.
End, Nicole et al.; "Het PHOX: a new class of easily prepared modular chiral ligands"; Tetrahedron Asymmetry, vol. 15, pp. 2235-2239, 2004.
Germany Office Action dated Feb. 11, 2010, issued in corresponding Germany Patent Application No. 102008033164.3.
Imamoto, Tsuneo et al.; "Highly enantioselective hydrosilylation of simple ketones catalyzed by rhodium complexes of P-chiral diphosphine ligands bearing tert-butylmethylphosphino groups"; Tetraedron: Asymmetry, vol. 17, 2006, pp. 560-565.
Trost, Barry M. et al., "Asymmetric Transition-Metal-Catalyzed Allylic Alkylations: Applications in Total Synthesis" Chem Rev, 103, pp. 2921-2943, 2003.
Trost, Barry M. et al. "Asymmetric Transition-Metal-Catalyzed Allylic Alkylations" Chem Rev, 96, pp. 395-422, 1996.

*Primary Examiner* — James O. Wilson
*Assistant Examiner* — Brian McDowell
(74) *Attorney, Agent, or Firm* — Westerman, Hattori, Daniels & Adrian, LLP

(57) ABSTRACT

Disclosed is a process of preparing an optically active allyl compound, e.g., as represented by formula (III):

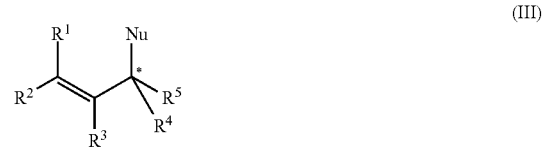

comprising asymmetrically coupling an allyl compound with an organic nucleophilic compound in the presence of a catalyst. The catalyst is preferably a transition metal complex compound having a phosphine ligand. The phosphine ligand is preferably a 2,3-bis(dialkylphosphino)pyrazine derivative. The pyrazine derivative is preferably a quinoxaline derivative. The transition metal is preferably palladium.

1 Claim, No Drawings

PROCESS OF PREPARING OPTICALLY ACTIVE ALLYL COMPOUND

TECHNICAL FIELD

This invention relates to a process of preparing an optically active allyl compound that is important as an intermediate for pharmaceuticals, agricultural chemicals, or physiologically active substances, for example, very useful as an intermediate for synthesizing antibiotics.

BACKGROUND ART

Processes that are known or thought to be useful for the production of an optically active allyl compound include (1) once synthesizing a racemic form of a desired allyl compound, followed by optical resolution using an optically active resolving agent or an enzyme, (2) starting with an asymmetric compound, or (3) using an asymmetric catalyst.

The process (1) which uses an optically active resolving agent requires an equivalent or more amount of a resolving agent relative to an allyl compound. Moreover, complicated procedures such as crystallization, separation, and purification, are involved before obtaining an optically active allyl compound. The process (1) which uses an enzyme, while capable of yielding an allyl compound with relatively high optical purity, limits the type of a reaction substrate and the absolute configuration of a resulting allyl compound.

The process (2) is conceivable but problematic in that an optically active starting compound is not only expensive but must be used in a stoichiometric excess.

As the process (3), detailed researches have recently been done into catalytic asymmetric synthesis of an optically active allyl compound that can achieve high efficiency and asymmetric yield, as reported in Trost, B. M. & Van Vranken, D. L. *Chem. Rev.*, 96, 395-422 (1996) and Trost, B. M. & Crawley, M. L., *Chem. Rev.*, 103, 2921-2944 (2003). The techniques in this line are still under study.

SUMMARY OF THE INVENTION

In the light of the above circumstances, it is an object of the invention to provide a process of preparing an optically active allyl compound at high efficiency in high asymmetric yield.

As a result of extensive studies on catalytic asymmetric synthesis of an optically active allyl compound, the present inventors have found that asymmetric coupling reaction of an allyl compound with an organic nucleophilic compound in the presence of a catalyst gives a desired optically active allyl compound with the reduced number of steps at high efficiency in good asymmetric yield. The present invention has been reached based on this finding.

The invention provides a process of preparing an optically active allyl compound represented by formula (III):

(III)

wherein $R^1$, $R^2$, $R^3$, $R^4$, and $R^5$ each represent a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, or a substituted aromatic heterocyclic group; Nu represents a nucleophilic group selected from an α-ketocarbanion group, an amino group, and a substituted amino group; and the asterisk * indicates an asymmetric center.

or an optically active allyl compound represented by formula (IV):

(IV)

wherein $R^1$, $R^2$, $R^3$, $R^4$, $R^5$, Nu, and * are as defined above.
or a mixture of the compound of formula (III) and the compound of formula (IV).

The process comprises asymmetrically coupling an allyl compound represented by formula (I):

(I)

wherein $R^1$, $R^2$, $R^3$, $R^4$, and $R^5$ are as defined above; and E represents a leaving group selected from a group comprising an oxygen atom and the group which is represented by $R^1$, $R^2$, $R^3$, $R^4$, and $R^5$ and is bonded to the oxygen atom; a halogeno group; a carbonic ester group; a sulfonic ester group; a phosphonic ester group; a phoshoric ester group; and a carboxylic ester group.
with an organic nucleophilic compound represented by formula (II):

Nu-H          (II)

wherein Nu is as defined above.
in the presence of a catalyst.

DETAILED DESCRIPTION OF THE INVENTION

The allyl compound that can be used as a starting material in the process of the invention is represented by formula (I). The product obtained by the process of the invention is the optically active allyl compound represented by formula (III), the optically active allyl compound represented by formula (IV), or a mixture thereof. The groups represented by $R^1$, $R^2$, $R^3$, $R^4$, and $R^5$ in formulae (I), (III), and (IV) will be described.

The term "alkyl group" includes straight-chain or branched alkyl groups having 1 to 6 carbon atoms, such as methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, and 5-methylpentyl.

The term "substituted alkyl group" includes the above recited alkyl groups at least one hydrogen atom of which is displaced with a substituent, such as an alkyl group, a cycloalkyl group, an alkoxy group, a halogen atom, an amino group, or a protected amino group. Any protective group known for the protection of an amino group can be used. Examples of the amino protective group are described, e.g., in *Protective Groups in Organic Synthesis*, 2nd Ed., John Wiley & Sons, Inc. Examples of useful amino protective groups include an alkyl group, a cycloalkyl group, an aralkyl group, an acyl group, and an alkyloxycarbonyl group.

The term "cycloalkyl group" includes a cycloalkyl group having 3 to 16 carbon atoms, such as cyclopropyl, cyclobutyl, cyclopentyl, cyclohexyl, cycloheptyl, 2-methylcyclopentyl, 3-methylcyclopentyl, cycloheptyl, 2-methylcyclohexyl, 3-methylcyclohexyl, and 4-methylcyclohexyl. The term "cycloalkyl group" also includes a polycyclic alkyl group, such as menthyl, bornyl, norbornyl, or adamantyl.

The substituted cycloalkyl group includes the above described cycloalkyl groups at least one hydrogen atom of which is displaced with a substituent such as an alkyl group, a cycloalkyl group, an alkoxy group, a halogen atom, an amino group or a protected amino group.

The term "aralkyl group" includes aralkyl groups having 7 to 12 carbon atoms, such as benzyl, 2-phenylethyl, 1-phenylpropyl, 2-phenylpropyl, 3-phenylpropyl, 1-phenylbutyl, 2-phenylbutyl, 3-phenylbutyl, 4-phenylbutyl, 1-phenylpentyl, 2-phenylpentyl, 3-phenylpentyl, 4-phenylpentyl, 5-phenylpentyl, 1-phenylhexyl, 2-phenylhexyl, 3-phenylhexyl, 4-phenylhexyl, 5-phenylhexyl, and 6-phenylhexyl.

The substituted aralkyl group includes the above described aralkyl groups at least one hydrogen atom of which is displaced with a substituent such as an alkyl group, a cycloalkyl group, a halogenated alkyl group, an alkoxy group, a halogen atom, an amino group, or an alkyl-substituted amino group.

The term "aryl group" includes aryl groups having 6 to 14 carbon atoms, such as phenyl, naphthyl, and anthryl.

The substituted aryl group includes the above described aryl groups at least one hydrogen atom of which is displaced with a substituent such as an alkyl group, a cycloalkyl group, a halogenated alkyl group, an alkoxy group, a halogen atom, an amino group, or an alkyl-substituted amino group and the above described aryl groups adjacent two hydrogen atoms of which are displaced with a substituent such as an alkylenedioxy group.

The "aliphatic heterocyclic group" is preferably 5- or 6-membered. The aliphatic heterocyclic group includes one containing 1 to 3 hetero atoms such as nitrogen, oxygen, and sulfur atoms. Examples of the aliphatic heterocyclic group include pyrrolidy-2-one, piperidino, piperazinyl, morpholino, tetrahydrofuryl, and tetrahydropyranyl.

The term "substituted aliphatic heterocyclic group" includes the above described aliphatic heterocyclic groups at least one hydrogen atom of which is displaced with a substituent such as an alkyl group, a cycloalkyl group, a halogenated alkyl group, an alkoxy group, or a halogen atom.

The term "aromatic heterocyclic group" preferably includes 5- or 6-membered, monocyclic or polycyclic aromatic heterocyclic rings containing 1 to 3 hetero atoms such as nitrogen, oxygen, and sulfur atoms. Examples of the aromatic heterocyclic group include pyridyl, imidazolyl, thiazolyl, furfuryl, pyranyl, furyl, benzofuryl, and thienyl.

The "substituted aromatic heterocyclic group" includes the above described aromatic heterocyclic groups at least one hydrogen atom of which is displaced with a substituent such as an alkyl group, a cycloalkyl group, a halogenated alkyl group, an alkoxy group, or a halogen atom.

In formulae (I), (III), and (IV), $R^1$, $R^2$, $R^3$, $R^4$, and $R^5$ may be the same or different. They may be independent of each other, or two or more of them may be crosslinked to each other.

In formula (I), E represents a leaving group. Specifically E represents a group comprising (a) a hydrogen atom or the group represented by $R^1$, $R^2$, $R^3$, $R^4$, and $R^5$, and (b) an oxygen atom. In this case E is bonded to the carbonyl group via the oxygen atom. E also represents a halogeno group, a carbonic ester group, a sulfonic ester group, a phosphonic ester group, a phosphoric ester group, and a carboxylic ester group.

Examples of the group comprising the hydrogen atom or the group as represented by $R^1$, $R^2$, $R^3$, $R^4$, or $R^5$ and an oxygen atom include a hydroxyl group, a methoxy group, an ethoxy group, a phenyloxy group, a benzyloxy group, and a p-methoxybenzyloxy group. Examples of the halogeno group are fluoro, chloro, bromo, and iodo. Examples of the carbonic ester are methyl carbonate, ethyl carbonate, and tert-butyl carbonate. Examples of the sulfonic ester are a methanesulfonate, a benzenesulfonate, a p-toluenesulfonate, and a trifluoromethanesulfonate. Examples of the phosphonic ester are methyl phosphonate, ethyl phosphonate, and phenyl phosphonate. Examples of the phosphoric ester are methyl phosphate, ethyl phosphate, and phenyl phosphate. Examples of the carboxylic ester include an acetate, a propionate, an oxalate, and a benzoate.

The organic nucleophilic compound represented by formula (II) that is used in the coupling reaction of the allyl compound of formula (I) is described below. The group represented by Nu in formula (II) is a nucleophilic group selected from an α-ketocarbanion group, an amino group, and a substituted amino group.

Examples of the α-ketocarbanion include organic compounds having a structure of formula as described below. Examples of such organic compounds include acetone α-dehydro anion, ethyl acetate α-dehydro anion, and diethyl malonate α-dehydro anion.

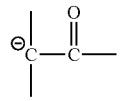

The term "substituted amino group" refers to an amino group at least one hydrogen of which is displaced with a substituent such as an alkyl group, a cycloalkyl group, a halogenated alkyl group, an alkoxy group, or a halogen atom. The term "substituted amino group" includes a cyclic amino group, such as a morpholino group, a pyrrolidino group, and a 3-oxazolin-2-on-1-yl group.

The coupling reaction between the allyl compound of formula (I) and the organic nucleophilic compound of formula (II) is carried out in the presence of a catalyst. In the present invention, a transition metal complex compound having a phosphine ligand is preferably used as a catalyst.

It is particularly preferred to use, as a phosphine ligand, a 2,3-bis(dialkylphosphino)pyrazine derivative represented by formula (V):

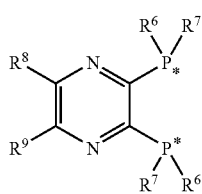

wherein * is as defined above; $R^6$ and $R^7$ each represent an alkyl group or a substituted alkyl group; $R^8$ and $R^9$ each have the same meaning as $R^1$, $R^2$, $R^3$, $R^4$, and $R^5$, or $R^8$ and $R^9$ are taken together to form a fused ring.

In formula (V), the alkyl group and the substituted alkyl group as $R^6$ and $R^7$ are exemplified by the same examples as recited for $R^1$, $R^2$, $R^3$, $R^4$, and $R^5$. $R^6$ and $R^7$ may be the same or different. Although $R^6$ and $R^7$ may be independent of each other or crosslinked to each other, it is essential to select $R^6$ and $R^7$ so as to result in asymmetry on the phosphorus atom or to make the phosphorus atom constitute a point of the symmetry plane of axial asymmetry.

In order to effectively induce asymmetry on the phosphorus atom, it is preferred that $R^6$ and $R^7$ are selected so as to make a large difference in three-dimensional bulkiness therebetween. Examples of a preferred combination of $R^6$ and $R^7$ are a combination of a methyl group and a tert-butyl group and a combination of a methyl group and an adamantyl group.

In order to make the phosphorus atom constitute a point of the symmetry plane of axial asymmetry, it is preferred that the moieties of $R^6$ and $R^7$ providing the asymmetry are as close as possible to the phosphorus atom so as to effectively induce the asymmetry. This is exemplified by a configuration in which $R^6$ and $R^7$ are crosslinked to each other, and an atomic group including the crosslinked moiety and the phosphorus atom is 2,5-dimethylphospholane.

The group represented by $R^8$ and $R^9$ in formula (V) is then described. As stated, $R^8$ and $R^9$ have the same meaning as $R^1$, $R^2$, $R^3$, $R^4$, and $R^5$. $R^8$ and $R^9$ may be the same or different. $R^8$ and $R^9$ may be taken together to form a fused ring. Examples of the fused ring include a benzene ring, a naphthalene ring, a phenanthrene ring, a methylenedioxy ring, an ethylenedioxy ring, and a cyclohexane ring.

It is particularly preferred that $R^8$ and $R^9$ are taken together to form a benzene ring. In this case, the pyrazine derivative represented by formula (V) is a 2,3-bis(dialkylphosphino)quinoxaline derivative represented by formula (VI):

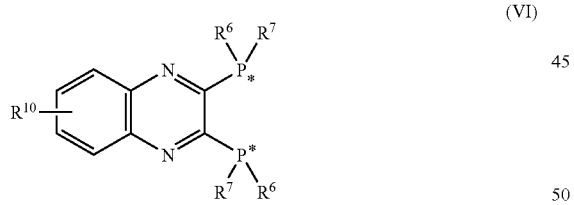

(VI)

wherein $R^6$, $R^7$, and the asterisk * are as defined above; and $R^{10}$ represents a substituent.

In formula (VI), the substituent represented by $R^{10}$ is a monovalent substituent. Examples of the monovalent substituent include an alkyl group, a cycloalkyl group, a halogenated alkyl group, an alkoxy group, a halogen atom, an amino group, a protected amino group, and a nitro group. The benzene ring may have one or more than one substituents $R^{10}$. When there are two or more substituents $R^{10}$, they may be either the same or different.

Examples of the pyrazine derivative of formula (V) having asymmetry introduced at the phosphorus atom are shown below.

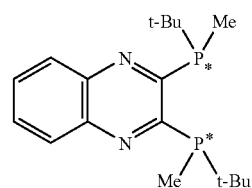

(a)

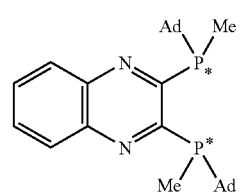

(b)

(a): (S,S)-2,3-Bis(tert-butylmethylphosphino)quinoxaline or (R,R)-2,3-Bis(tert-butylmethylphosphino)quinoxaline (b): (S,S)-2,3-Bis(adamantylmethylphosphino)quinoxaline or (R,R)-2,3-Bis(adamantylmethylphosphino)quinoxaline Examples of the pyrazine derivative of formula (V) in which the phosphorus atom constitutes a point of symmetry plane of axial asymmetry as shown below.

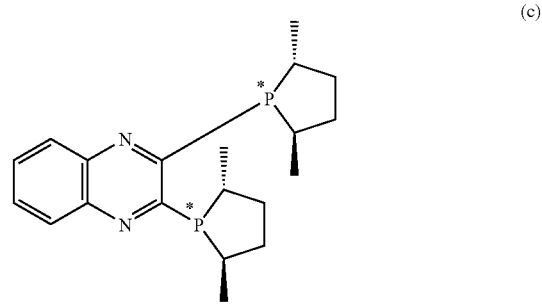

(c)

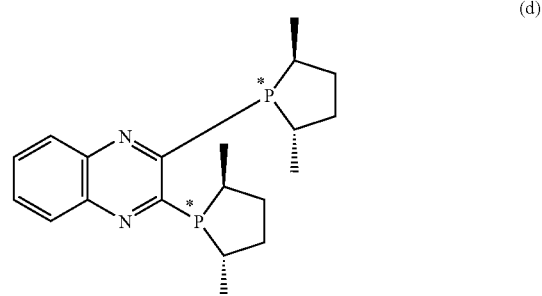

(d)

(c): 2,3-Bis[(R,R)-2,5-dimethylphospholano]quinoxaline (d): 2,3-Bis[(S,S)-2,5-dimethylphospholano]quinoxaline The pyrazine derivatives of formula (V) including the quinoxaline derivatives of formula (VI) can be prepared in accordance with the process disclosed in commonly assigned U.S. Patent Application 2007/0021610A1, the disclosure of which is incorporated herein by reference.

The pyrazine derivative of formula (V) including the quinoxaline derivative of formula (VI) reacts with a transition metal to form a complex compound, which can be used as a catalyst for asymmetric synthesis. Examples of the transition metal with which to form a complex include rhodium, ruthenium, iridium, palladium, nickel, and iron. Preferred of them are the group VIII elements, such as rhodium, ruthenium, iridium, palladium, and nickel. Palladium is particularly preferred. A palladium complex having the pyrazine derivative of formula (V) as a ligand can be prepared by, for example, mixing a pyrazine derivative of formula (V) and a palladium compound having an allyl compound coordinated to a palladium atom, e.g., $[PdCl(\eta^3-C_3H_5)]_2$.

The catalyst comprising the transition metal complex compound is preferably used in an amount of 0.0001 to 100 mol %, more preferably 0.001 to 10 mol %, based on the reaction substrate. To promote the reaction moderately while suppressing the amount of the catalyst to be used, an even more preferred amount of the catalyst to be used is 0.02 to 5 mol %.

To accelerate smooth progress of the asymmetric coupling reaction, a base may be used. Examples of useful bases include, but are not limited to, N,O-bis(trimethylsilyl)acetamide (BSA), potassium acetate, and a mixture thereof.

The asymmetric coupling reaction is usually carried out in a solvent commonly employed in general organic chemical reactions, such as toluene, hexane, tetrahydrofuran (THF), diethyl ether, dioxane, acetone, ethyl acetate, chlorobenzene, dimethylformamide (DMF), acetic acid, and water. Preferred solvents are methanol, ethanol, and dichloromethane.

The amount of the solvent to be used is decided appropriately, taking into consideration the fluidity of the reaction mixture during the reaction and the effects the solvent exerts on the reaction. Where the reaction proceeds well without a solvent, for example, when the reactant mixture to be reacted is a low-viscosity, homogeneous fluid with no aid of a solvent, it is not necessary to use a solvent.

The asymmetric coupling reaction temperature is preferably −80° C. to 150° C., more preferably 0° C. to 120° C. in which range the reaction is promoted while suppressing a side reaction and racemization.

The asymmetric coupling reaction is preferably carried out for a period of from one minute to one month, more preferably a period of from 3 hours to 3 days, which period is adequate for completion of the reaction.

The asymmetric coupling reaction according to the present invention generally results in the formation of the optically active allyl compound of formula (III). When rearrangement of the leaving group occurs during the reaction, the optically active allyl compound of formula (IV) is obtained. When it is desired to selectively obtain either one of them, reaction conditions that will result in an increased selectivity to a desired compound are established through proper selection of the catalyst, the solvent, and the like. Otherwise, a mixture of the two compounds as obtained can be subjected to crystallization, distillation, column chromatography, preparative HPLC, and so forth to isolate a desired optically active allyl compound.

The optically active allyl compound synthesized by the process of the invention can be used in the form of a reaction mixture as obtained. If desired, the reaction mixture may be subjected to usual work-up and purification procedures such as solvent removal, liquid-liquid separation, crystallization, distillation, sublimation, and column chromatography.

The preparation process of the invention may be performed either batchwise or continuously.

The optically active allyl compound obtained by the process of the invention is used as an intermediate for pharmaceuticals, agricultural chemicals, and physiologically active substances. For example, it is useful as an intermediate for synthesis of antibiotics.

EXAMPLES

The present invention will now be illustrated in greater detail with reference to Examples, but it should be understood that the invention is not construed as being limited thereto.

All the synthesis operations in Examples were carried out using thoroughly dried glassware. The reaction was performed in an argon or nitrogen atmosphere. A commercially available phosphine ligand, (R,R)-2,3-bis(tert-butylmethylphosphino)-quinoxaline ((R,R)-t-Bu-QuinoxP*), from Sigma-Aldrich Japan, was used as such. The solvent and the metal compound such as $[PdCl(\eta^3-C_3H_5)]_2$ were general reagents.

NMR spectrum measurement was performed using an NMR spectrometer from JEOL, Ltd. ($^1H$: 300 MHz; $^{13}C$: 75.4 MHz; $^{31}P$: 121.4 MHz). Tetramethylsilane ($^1H$) was used as an internal standard. GC analysis was performed using GC-14B FID detector from Shimadzu Corp. Mass spectrometry was conducted using GC-MS from Shimadzu Corp.

Example 1

Synthesis of dimethyl (S)-α-(1,3-diphenyl-2-propen-1-yl)malonate

In 0.5 ml of dichloromethane were suspended 0.9 mg (2.5 μmol) of $[PdCl(\eta^3-C_3H_5)]_2$ and 1.8 mg (5.5 μmol) of (R,R)-t-Bu-QuinoxP* (1), followed by stirring at room temperature for 10 to 30 minutes. To the resulting solution were added a solution of 126 mg (0.50 mmol) of 1,3-diphenyl-2-propenyl acetate in 1.5 ml of dichloromethane, 171 μl (1.50 mmol) of dimethyl malonate, 367 μl (1.50 mmol) of N,O-bis(trimethylsilyl)acetamide (BSA), and a trace amount of potassium acetate. The reaction system was stirred at room temperature for 1 hour. The reaction mixture was diluted with diethyl ether, and a saturated aqueous solution of ammonium chloride was added to stop the reaction. The resulting mixture was extracted with diethyl ether, and the organic layer was washed with a sodium chloride aqueous solution. The organic layer was dried over anhydrous sodium sulfate. Any volatile matter was evaporated off, and the residue was purified by silica gel column chromatography.

Examples 2 to 13

Various optically active allyl compounds were synthesized in the same manner as in Example 1, except for altering the nucleophilic compound (Nu-H), additive, and so forth as shown in Table 1 below. The results obtained are shown in Table 1 together with the results of Example 1. Unless otherwise specified, the allylalkylation reaction system was 1,3-diphenyl-2-propenyl acetate (3)/malonic ester or acetylacetone/BSA/t-Bu-QuinoxP* (1)/$[PdCl(\eta^3-C_3H_5)]_2$/$CH_2Cl_2$=0.50 mmol/1.5 mmol/1.5 mmol/0.0055 mmol/0.0025 mmol/2.0 ml; 0.1 mol % Pd, and the allylamination reaction system was 1,3-diphenyl-2-propenyl acetate (3)/amine/BSA/t-Bu-QuinoxP* (1)/$[PdCl(\eta^3-C_3H_5)]_2$/$CH_2Cl_2$=0.50 mmol/1.5 mmol/1.5 mmol/0.011 mmol/0.0050 mmol/2.0 ml; 2 mol % Pd.

TABLE 1

Synthesis of Optically Active Allyl Compound

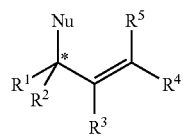

1 (R,R)-t-Bu-Quinox P*

| Example No. | Nu-H | Additive | Amount of Catalyst (mol % Pd) | Temp. (°C.) | Time (hr) | Yield[1] (%) | % ee[2] (Abs. Config.)[3] |
|---|---|---|---|---|---|---|---|
| 1 | $H_2C(COOMe)_2$ | KOAc + BSA | 1 | r.t. | 1 | 85 (4a) | 92 (S) |
| 2 | $HCCH_3(COOMe)_2$ | KOAc + BSA | 1 | r.t. | 1 | 97 (4b) | 95 (R) |
| 3 | $HC(n-Bu)(COOEt)_2$ | KOAc + BSA | 1 | r.t. | 1 | 87 (4c) | 92 |
| 4 | $HC(CH_2Ph)(COOEt)_2$ | KOAc + BSA | 1 | r.t. | 48 | 93 (4d) | 90 |
| 5 | $HC(NHCHO)(COOEt)_2$ | KOAc + BSA | 1 | r.t. | 26 | 94 (4e) | 91 |
| 6 | $HC(NHAc)(COOEt)_2$ | KOAc + BSA | 1 | r.t. | 27 | 83 (4f) | 91 (R) |
| 7 | $H_2C(COMe)_2$ | KOAc + BSA | 1 | r.t. | 1 | 88 (4g) | 95 (S) |
| 8[4] | $HCCH_3(COOMe)_2$ | KOAc + BSA | 3 | −50° C. | 20 | 92 (4b) | 98.7 (R) |
| 9 | morpholine | — | 2 | r.t. | 13 | 69 (4h) | 78 |
| 10 | morpholine | BSA | 2 | r.t. | 13 | 94 (4h) | 89 |
| 11 | pyrrolidine | BSA | 2 | r.t. | 20 | 81 (4i) | 90 (R) |
| 12 | butylamine | BSA | 2 | r.t. | 63 | >99 (4j) | 73 |
| 13[5] | cyclohexylamine | BSA | 4 | r.t. | 48 | 96 (4k) | 89 |

Note:
[1] Isolation yield
[2] Determined by chiral HPLC
[3] Determined by comparing the chiral HPLC results with literature data.
[4] Reaction system was 1,3-diphenyl-2-propenyl acetate (3)/methyl malonate/BSA/t-Bu-QuinoxP* (1)/[PdCl(η³-C₃H₅)]₂/CH₂Cl₂ = 0.50 mmol/1.5 mmol/1.5 mmol/0.016 mmol/0.0075 mmol/2.0 ml; 3 mol % Pd
[5] Reaction system was 1,3-diphenyl-2-propenyl acetate (3)/cyclohexylamine/BSA/t-Bu-QuinoxP* (1)/[PdCl(η³-C₃H₅)]₂/CH₂Cl₂ = 0.50 mmol/1.5 mmol/1.5 mmol/0.021 mmol/0.010 mmol/1.0 ml; 4 mol % Pd According to the process of the present invention, an optically active allyl compound with high optical purity can be produced with the reduced number of steps using a small amount of a catalyst, and the catalyst used in the process achieves excellent catalytic activity and enantio- and diastereoselectivity. The optically active allyl compound obtained by the process of the invention is important as an intermediate for pharmaceuticals, agricultural chemicals, and physiologically active substances. For example, it is very useful as an intermediate for synthesizing antibiotics. Thus, the present invention is of very high industrial utility.

What is claimed is:

1. A process of preparing an optically active allyl compound represented by formula (III):

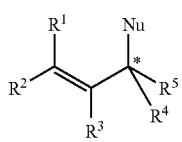

wherein $R^1$, $R^3$, and $R^4$ each represent a hydrogen atom; $R^2$ and $R^5$ each represent a phenyl group; Nu represents a nucleophilic group selected from an α-ketocarbanion group, an amino group, and a substituted amino group; and the asterisk * indicates an asymmetric center, or an optically active allyl compound represented by formula (IV):

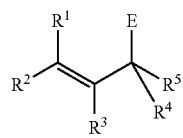

wherein $R^1$, $R^2$, $R^3$, $R^4$, $R^5$, Nu, and * are as defined above, or a mixture of the compound of formula (III) and the compound of formula (IV), the process comprising asymmetrically coupling an allyl compound represented by formula (I):

(I)

wherein $R^1$, $R^2$, $R^3$, $R^4$, and $R^5$ are as defined above; and E represents a leaving group which is a carboxylic ester group, with an organic nucleophilic compound represented by formula (II):

Nu-H  (II)

wherein Nu is as defined above, in the presence of a Pd complex compound catalyst having a quinoxaline derivative represented by formula (a) as a ligand:

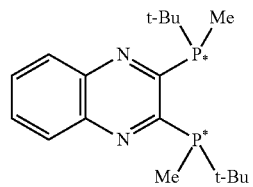
(a)

wherein * is as defined above.

* * * * *